United States Patent
Hatzistergos et al.

(10) Patent No.: US 8,347,741 B2
(45) Date of Patent: Jan. 8, 2013

(54) SPECIMEN HANDLING APPARATUS

(75) Inventors: Michael Hatzistergos, Beacon, NY (US); Jonathan Levy, Poughkeepsie, NY (US); Christopher Michael Molella, Poughkeepsie, NY (US); Paul Andrew Ronsheim, Hopewell Junction, NY (US); Dmitriy Shneyder, Hopewell Junction, NY (US); Vincent Vazquez, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 241 days.

(21) Appl. No.: 12/791,248

(22) Filed: Jun. 1, 2010

(65) Prior Publication Data

US 2011/0290039 A1    Dec. 1, 2011

(51) Int. Cl.
*G01N 1/00*   (2006.01)
(52) U.S. Cl. ......................................... 73/863
(58) Field of Classification Search .............. None
See application file for complete search history.

(56) References Cited

U.S. PATENT DOCUMENTS

| | | | |
|---|---|---|---|
| 4,768,911 | A | 9/1988 | Balter |
| 5,105,932 | A | 4/1992 | Bryson, III et al. |
| 6,002,136 | A | 12/1999 | Naeem |
| 6,388,262 | B1 | 5/2002 | Alani et al. |
| 7,041,985 | B1 | 5/2006 | Wang et al. |
| 7,291,847 | B2 | 11/2007 | Morrison |
| 7,423,263 | B2 | 9/2008 | Hong et al. |
| 7,542,136 | B2 | 6/2009 | Zangooie et al. |
| 7,586,616 | B2 * | 9/2009 | Ran et al. ............ 356/445 |
| 2009/0146075 | A1 | 6/2009 | Schmid et al. |

* cited by examiner

*Primary Examiner* — Robert R Raevis
(74) *Attorney, Agent, or Firm* — Cantor Colburn LLP; Ian MacKinnon

(57) ABSTRACT

A specimen handling apparatus is provided and includes a body in which a bore is defined and a needle having a tip portion and a bit, which is removably insertible into the bore with the tip portion at least partially exposed, the bore and the bit each being formed such that, when the bit is inserted into the bore, the needle is forced into one of first or second rotational positions relative to a long axis thereof.

19 Claims, 4 Drawing Sheets

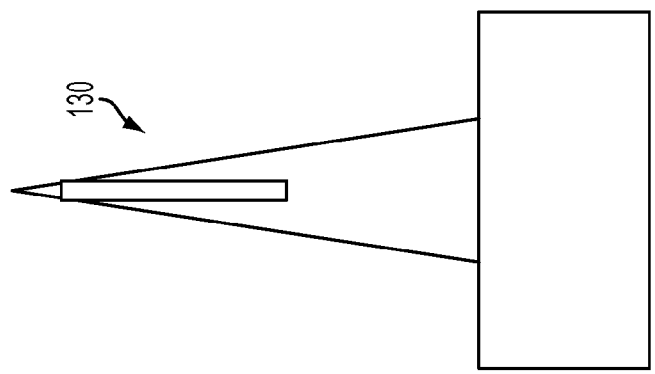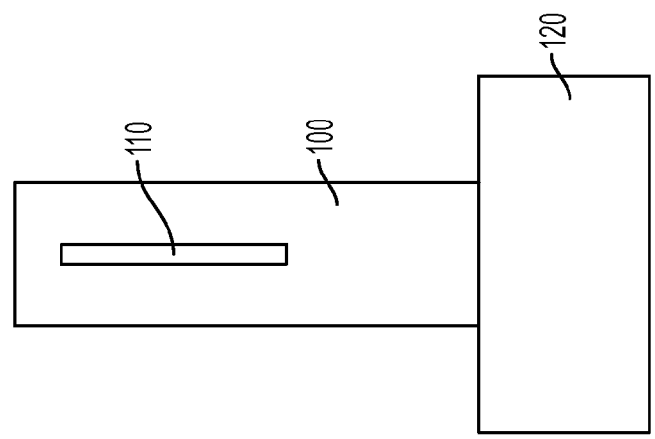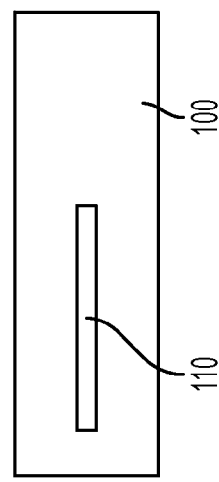
FIG. 1

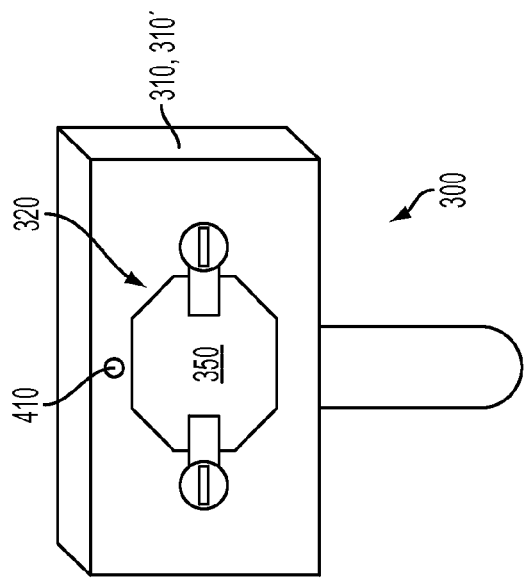
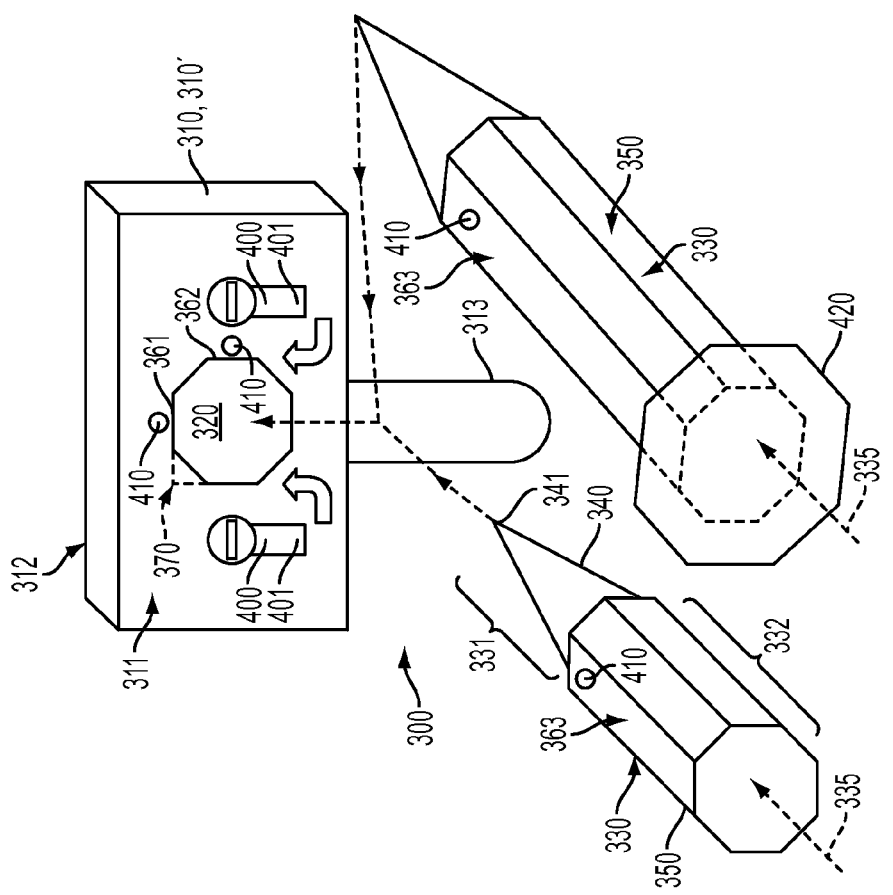

SPECIMEN HANDLING APPARATUS

BACKGROUND

Aspects of the present invention are directed to an apparatus for specimen handling during specimen preparation and analysis.

In manufacturing operations, very small components are often required to be analyzed via various analytical techniques. These techniques may include Transmission Electron Microscopy (TEM), Atom Probe Tomography (APT), Scanning Electron Microscopy (SEM), Focused Ion Beam (FIB), Scanning Probe Microscopy (SPM) and optical microscopy, amongst others and may be employed in various industrial and/or academic environments. In all cases, a high level of accuracy and precision in specimen manipulation is typically required.

A problem exists, however, in that the currently used apparatuses for specimen handling do not have accurate or precise specimen positioning systems. As such, the required high level of accuracy and precision in specimen handling is either unattained leading to specimen misalignment or attained only after several time consuming iterative corrections.

The lack of accuracy and precision provided by the currently used apparatuses may be caused by various factors. These include, but are not limited to, misalignment between a specimen and a holding device whereby the specimen is attached to the holding device at an angle as opposed to being straight on, a bend along the holding device and a rotation error whereby rotation of the holding device by a given angle for accurate specimen positioning cannot be guaranteed.

For example, in current apparatuses a flip stage is employed to rotate a specimen. Specimen alignment must be highly accurate lest the specimen be mounted improperly on the mounting. In the flip stage, the specimen is attached to a needle which is held between two plates. A back end of the needle is bent downwards to identify a first rotational position. With the needle in the first rotational position, an image of the specimen is taken such that its position can be determined. The needle is rotated toward a second rotational position such that the bent end now faces, for example, sideways to identify a 90° rotation. With the needle in the second rotational position, the specimen image is again taken such that its position can be re-determined. At this point, if the second specimen position is not horizontal, it can be inferred that the specimen is misaligned and that correction is required.

In the above-described scenario, the correction is time consuming and expensive. In addition, however, the flip stage itself may be highly inaccurate. The bending of the back of the needle can bend or damage the front end. Also, in order to be bent, the needle must be fashioned narrowly or otherwise less rigidly than it would otherwise be such that a risk of needle bending is increased. Finally, the bending itself along with the rotation are achieved by technicians who are prone to error.

SUMMARY

In accordance with an aspect of the invention, a specimen handling apparatus is provided and includes a body in which a bore is defined and a needle having a tip portion and a bit, which is removably insertible into the bore with the tip portion at least partially exposed, the bore and the bit each being formed such that, when the bit is inserted into the bore, the needle is forced into one of first or second rotational positions relative to a long axis thereof.

In accordance with another aspect of the invention, a specimen handling apparatus is provided and includes a body in which a bore is defined and a needle having a tip portion and a bit, which is removably insertible into the bore with the tip portion at least partially exposed, the bore being formed with at least three faces whose respective planes define a crossing that extends substantially in parallel with a long axis of the needle, and the bit being formed with at least one face such that, when the bit is inserted into the bore, the at least one bit face abuts one of the at least two bore faces to force the needle into one of first or second rotational positions relative to the long axis thereof.

In accordance with another aspect of the invention, a specimen handling apparatus is provided and includes a body in which a bore is defined and a needle having a tip portion and a bit, which is removably insertible into the bore with the tip portion at least partially exposed, the bore being formed with 3+n faces, where n is a non-negative integer, cooperatively defining a polygonal volume with adjacent faces forming edges that extend substantially in parallel with a long axis of the needle, and the bit having a shape substantially similar to the polygonal volume such that, when the bit is inserted into the bore, bit faces each abut one of the bore faces to force the needle into one of 3+n rotational positions, where n is a non-negative integer, relative to the long axis thereof.

In accordance with another aspect of the invention, a method of operating a specimen handling apparatus is provided and includes removably inserting a multifaceted bit of a needle into a multifaceted bore of a body such that the needle occupies a first rotational position defined by an abutment of at least one bit face and at least one bore face and such that a tip portion of the needle remains exposed, determining an initial position of the tip portion, rotating the needle about a long axis thereof such that the needle occupies a second rotational position defined by an abutment of at least one bit face and at least one other bore face and such that the tip portion remains exposed and verifying that a final position of the tip portion is substantially similar to the initial position.

BRIEF DESCRIPTIONS OF THE SEVERAL VIEWS OF THE DRAWINGS

The subject matter regarded as the invention is particularly pointed out and distinctly claimed in the claims at the conclusion of the specification. The foregoing and other aspects, features, and advantages of the invention are apparent from the following detailed description taken in conjunction with the accompanying drawings in which:

FIG. 1 is a diagram illustrating a series of specimen handling operations;

FIG. 3 is a perspective view of components of an apparatus for specimen handling;

FIG. 4 is a perspective view of the components of FIG. 3 having been brought together;

DETAILED DESCRIPTION

In accordance with aspects of the present invention, an apparatus for specimen handling is provided and allows for relatively accurate and precise specimen positioning. As will be described below, the apparatus reduces the likelihood of specimen misalignment, is substantially straight and provides for specimen rotation at repeatable given angles.

Figure 2:
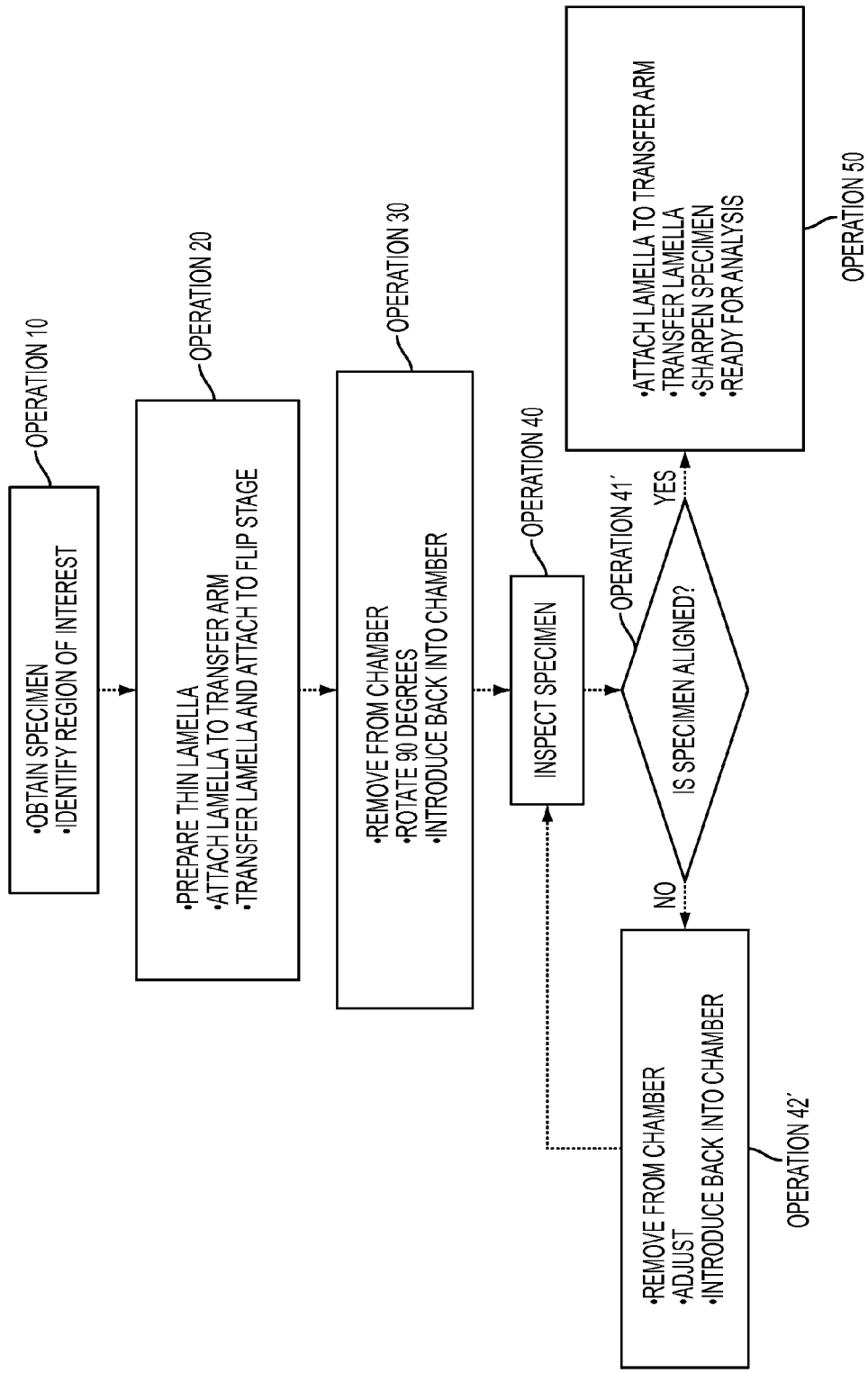
FIG. 2 is a schematic flow chart explaining specimen handling operations.

With reference to FIGS. 1 and 2, specimen preparation often begins with the obtaining of a specimen, such as a section of a silicon chip, and identification of a region of interest (ROI) 110 within that specimen (operation 10). A thin lamella 100 is then prepared (operation 20). Lamella 100 preparation includes cutting the lamella 100 from the specimen such that the lamella 100 includes the ROI 110, attaching the lamella 100 to a transfer arm and transferring the lamella 100 to a flip stage.

The flip stage and the lamella 100 are then removed from, e.g., an FIB vacuum chamber, rotated about a longitudinal axis of the flip stage and/or the lamella 100 by a given amount, such as 90°, 60° or 45°, and introduced back into the FIB vacuum chamber (operation 30). The position of the lamella 100 is then inspected (operation 40) and, if the lamella 100 is found to be properly aligned, the lamella 100 is reattached to a transfer arm, transferred onto the mounting 120 where it can be sharpened into a specimen for further study 130 with the ROI 110 at the tip (operation 50).

In current apparatuses, the re-inspection of the lamella 100 at operation 40 may indicate that the lamella 100 was misaligned (operation 41') and, in these cases, sharpening of the lamella 100 would destroy or substantially reduce a size of the ROI 110. Thus, the lamella 100 would have to be removed from the FIB vacuum chamber, adjusted for further re-inspection and introduced back into the FIB vacuum chamber (operation 42'). This process would continue until the lamella 100 was found to be properly aligned. In accordance with aspects of the present invention, lamella 100 misalignment is prevented or substantially reduced such that operations 41' and 42' are no longer necessary.

With reference to FIGS. 3 and 4, a specimen handling apparatus 300 is provided and includes a body 310 and a needle 330. The body 310 has first and second opposing faces 311 and 312 and a handle 313. A multifaceted bore 320 is defined through the body 310 and extends, in some embodiments, from the first face 311 to the second face 312. In other embodiments, the bore 320 is simply recessed into the body 310.

The needle 330 has a first axial section 331 and a second axial section 332. The first and second axial sections 331, 332 are disposed adjacent to and in-line with one another such that the needle 330 is substantially straight along its longitudinal axis 335 from a distal end of the first axial section 331 to an opposite distal end of the second axial section 332. The straightness of the needle 330 permits the needle to be fashioned more rigidly and/or wider than those of current apparatuses, which need to be bendable as described above. As such, the likelihood that the needle 330 will be straight and remain so along the longitudinal axis 335 is increased as compared to current apparatus needles.

A tip portion 340 is formed at the first axial section 331. The tip portion 340 is tapered along the longitudinal axis 335 and substantially conical in some embodiments. A point 341 may be formed at the distal end of the tip portion 340 and may be attachable to a specimen via adhesive, such as a metallic material deposited in an FIB. A multifaceted bit 350 is formed at the second axial section 332 and is removably insertible into the multifaceted bore 320 (see FIG. 4) such that the tip portion 340 remains at least partially exposed.

The multifaceted bore 320 is formed with at least two faces 361 and 362 whereas the multifaceted bit 350 is formed with at least one face 363. The respective planes of the bore faces 361, 362 define a linear crossing 370 that extends substantially in parallel with the longitudinal axis 335. When the multifaceted bit 350 is inserted into the multifaceted bore 320, the at least one bit face 363 is forced to abut with flush contact with one of the at least two bore faces 361 or 362. The abutment of the at least one bit face 363 and the at least two bore faces 361 and 362 is face-to-face abutment in that respective planes of each are adjacent to one another, in close contact and substantially parallel.

With the above described or other similar constructions, rotation of the multifaceted bit 350 relative to the multifaceted bore 320 is prevented or at least substantially impeded by mechanical and non-frictional interference between the multifaceted bit 350 and the multifaceted bore 320. Here, frictional interference refers to friction that may arise were at least one of the multifaceted bit 350 and multifaceted bore 320 circular with the two tightly fit together and the multifaceted bit 350 rotated by an unspecified degree. Mechanical and non-frictional interference, on the other hand, is generated from the flush contact abutment of the at least one bit face 363 with the one of the at least two bore faces 361 or 362. Thus, while the multifaceted bit 350 could be rotated by an unspecified degree in the presence of even extremely large frictional forces, no amount of rotation is permitted by the mechanical and non-frictional interference actually present between the multifaceted bit and the multifaceted bore unless one or the other is configured to mechanically give, as will be described below with reference to FIGS. 5 and 6.

The abutment forces the needle 330 as a whole to occupy a first rotational position relative to the longitudinal axis 335. The first rotational position is established in accordance with the plane of the one bore face 361 or 362 the bit face 363 contacts. Similarly, when the multifaceted bit 350 is inserted into the multifaceted bore 320 such that the at least one bit face 363 is forced to abut with the other bore face 361 or 362, the abutment forces the needle 330 as a whole to occupy a second rotational position relative to the longitudinal axis 335. The second rotational position is established in accordance with the plane of the other bore face 361 or 362. The first and second rotational positions are rotated from one another by a degree substantially similar to that of the at least two bore faces 361 and 362.

With the above arrangement, the first and second rotational positions of the needle 330 are rotationally displaced from one another by the angle of the linear crossing 370. That is, if the angle of the linear crossing 370 is 90°, 60° or 45°, the first and second rotational positions of the needle 330 will be rotated 90°, 60° or 45° from one another. The accuracy and precision of this rotation is, therefore, unrelated to the specimen handling skills of a technician.

In accordance with embodiments of the invention, the multifaceted bore 320 may define a regular polygonal volume therein with 3+n sides, where n is a non-negative integer (i.e., n={0, 1, 2, 3, ...}). Thus, in examples in which n=1, 3 or 5, the multifaceted bore 320 has 4, 6 or 8 faces and defines a squared volume, a hexagonal volume or an octagonal volume, respectively. The multifaceted bit 350 may be formed with a shape that is substantially similar to that of the multifaceted bore 320. As such, if the multifaceted bore 320 is squared, the multifaceted bit 350 is also squared, and so on.

Where the multifaceted bore 320 and the multifaceted bit 350 are squared, the first and second rotational positions are rotated 90 from one another and specimen positioning can be easily and relatively quickly verified by rotating the needle 330 from one position to the other with the specimen attached to the tip portion 340. Meanwhile, where the multifaceted bore 320 and the multifaceted bit 350 are hexagonal or octagonal, even greater positional accuracy is possible as more positional testing is possible.

The regularity of the polygonal volume refers to the fact that the polygonal volume includes end portions that are parallel with one another such that edges of the end portions at each face have right-angles and the faces all have substantially the same dimensions. However, it is noted that polygonal regularity is merely exemplary and that the volume formed by the multifaceted bore 320 and the multifaceted bit 350 may be irregular.

Further, although the multifaceted bit 350 is described above as having a same number of faces as the multifaceted bore 320, this is also merely exemplary and it is understood that embodiments exist in which the multifaceted bit 350 and the multifaceted bore 320 have different numbers of faces. For example, where the multifaceted bore 320 is squared and first and second rotational positions are required, the multifaceted bit 350 could be formed in various shapes both regular and irregular as long as rotation between the first and second positions can be completed with accuracy and repeatability. Thus, in some embodiments, the multifaceted bit 350 may be triangular, squared, pentagonal, hexagonal or octagonal whereas, in other embodiments, the multifaceted bit 350 may have, for example, a partially-circular shape with a chordal face that securely abuts the faces of the multifaceted bore 320.

The specimen handling apparatus 300 may include a locking element 400 to at least temporarily lock the multifaceted bit 350 in the multifaceted bore 320. As shown in FIGS. 3 and 4, the locking element 400 may include plates 401 that are screwed into the body 310 and rotatable between unlocked and locked positions. In the unlocked position, the plates 401 are removed from a profile of the multifaceted bore 320 whereas, in the locked position, the plates 401 prevent withdrawal of the multifaceted bit 350 from the multifaceted bore 320.

Reference markings 410 may be placed on the body 310 and the needle 330 to assist a technician in lining up the needle 330 with the first and second rotational positions. For example, as shown in FIG. 3, the reference markings identify one face of the multifaceted bit 350 and only two faces of the multifaceted bore 320. Thus, by lining up the reference markings of the multifaceted bit 350 and the multifaceted bore 320, a technician can avoid rotating the needle into 4 unmarked rotational positions.

As shown in FIG. 3, the needle 330 may further include a flange 420, which is wider than both the multifaceted bit 350 and the multifaceted bore 320. This flange 420 permits insertion of the needle 330 into and through the body 310 up to a certain axial position at which the flange 420 abuts the body 310 but not further. The flange 420 may be employed with or without the locking element 400.

Figure 5:
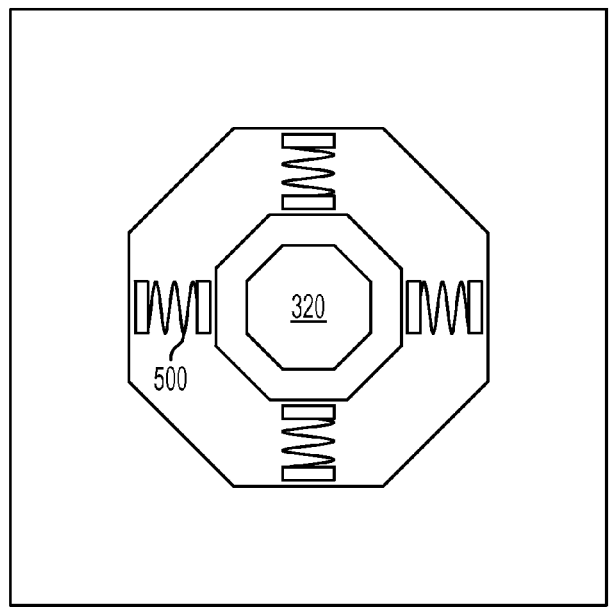
FIG. 5 is a view of the apparatus of FIGS. 3 and 4 according to further embodiments of the invention.
Figure 6:
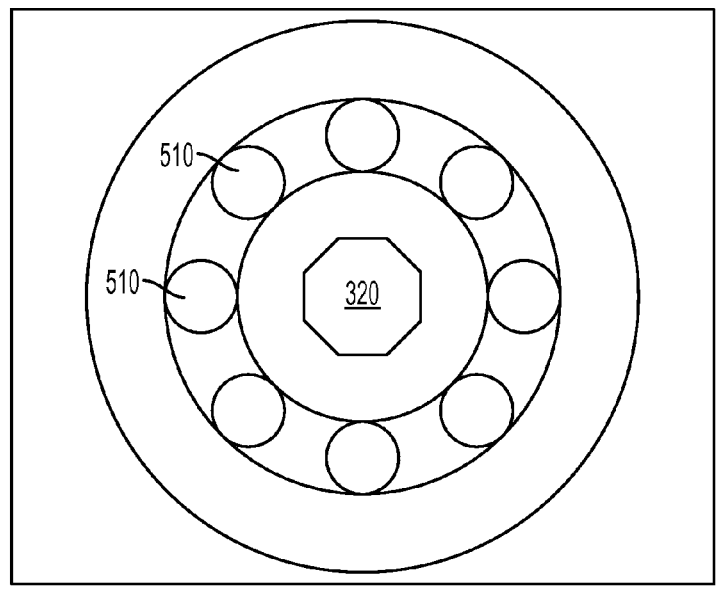
FIG. 6 is another view of the apparatus of FIGS. 3 and 4 according to the further embodiments of the invention.

With reference now to FIGS. 5 and 6, the specimen handling apparatus 300 may be configured such that the multifaceted bore 320 permits incremental rotation of the multifaceted bit 350 while the multifaceted bit 350 is inserted within the multifaceted bore 320. As such, rotation of the specimen attached to the needle 330 can be conducted within an imaging and analyzing device. As shown in FIG. 5, the faces of the multifaceted bore 320 may be spring-loaded by elastic elements 500, such as springs or coils. Similarly, as shown in FIG. 6, the multifaceted bit 350 may be rotatable supported by ball bearings 510. Here, the ball bearings 510 support the rotation of the multifaceted bit 350 while the spring loaded faces of the multifaceted bore 320 retract and recover as the faces of the multifaceted bit 350 move into and out of face-to-face abutment with the faces of the multifaceted bore 320.

In accordance with embodiments, the rotation of the multifaceted bit 350 may be done by hand in which case the specimen handling apparatus 300 needs to first be removed from an analytical chamber to perform the rotational operation. However, in the case of the ball bearings design, a motorized system can be attached to the needle 330 to allow for rotation remotely or, in this case, rotation without having to remove the apparatus from the analytical chamber.

In accordance with another aspect of the invention, a method of operating a specimen handling apparatus 300 is provided. The method includes removably inserting a multifaceted bit 350 of a needle 330 into a multifaceted bore 320 of a body 310 such that the needle 330 occupies a first rotational position defined by an abutment of at least one bit face 363 and at least one bore face 361 or 362 and such that a tip portion 340 of the needle 330 remains exposed. The method also includes determining an initial position of the tip portion 340, and rotating the needle 330 about a longitudinal axis 335 thereof such that the needle 330 occupies a second rotational position defined by an abutment of at least one bit face 363 and at least one other bore face 361 or 362 and such that the tip portion 340 remains exposed. Finally, the method includes verifying that a final position of the tip portion 340 is substantially similar to the initial position.

In accordance with this aspect, if the final position of the tip portion 340 is substantially similar to the initial position, it can be determined that the needle 330 is substantially straight along its longitudinal axis 335 and that, therefore, the needle 330 is usable for specimen handling operations.

In accordance with embodiments, the method may further include attaching a specimen to the tip portion 340. Here, the determining operation may alternatively or additionally include determining an initial position of the specimen and, in this case, the verifying includes verifying that a final position of the specimen is substantially similar to the initial position. If the final position of the specimen is substantially similar to the initial position, it can be determined that the specimen is substantially aligned and that, therefore, the specimen is mountable.

The method may include removing the multifaceted bit 350 from the multifaceted bore 320 prior to the rotating or, where the multifaceted bore 320 permits rotation of the inserted multifaceted bit 350, the rotating may be achieved with the multifaceted bit 350 inserted in the multifaceted bore 320.

The specimen handling apparatus 300 may further include at least one or more additional bodies 310' having multifaceted bores 320 that are compatible with the multifaceted bit 350. The additional bodies 310' may be similar in shape as the body 310 or differently shaped as long as the multifaceted bit 350 can be removably insertible therein.

While the disclosure has been described with reference to exemplary embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular exemplary embodiment disclosed as the best mode contemplated for carrying out this disclosure, but that the disclosure will include all embodiments falling within the scope of the appended claims.

What is claimed is:

1. A specimen handling apparatus, comprising:
a body in which a bore is defined; and
a needle having a tip portion, which is adhesively attachable to a silicon chip lamella, and a bit, which is removably insertible into the bore with the tip portion at least partially exposed,
the bore and the bit each being formed such that, when the bit is inserted into the bore, the needle is forced into one of first or second rotational positions relative to a long axis thereof from which needle rotation is impeded by non-frictional mechanical interference between the bit and the bore.

2. The specimen handling apparatus according to claim 1, wherein the bore and bit are both multifaceted.

3. The specimen handling apparatus according to claim 1, wherein the first and the second rotational positions are separated from one another by at least one of 90°, 60° or 45°.

4. The specimen handling apparatus according to claim 1, wherein the needle is incrementally rotatable between the first and second rotational positions while the bit is inserted in the bore.

5. A specimen handling apparatus, comprising:
a body in which a bore is defined; and
a needle having a tip portion, which is adhesively attachable to a silicon chip lamella, and a bit, which is removably insertible into the bore with the tip portion at least partially exposed,
the bore being formed with at least two faces whose respective planes define a crossing that extends substantially in parallel with a long axis of the needle, and
the bit being formed with at least one face such that, when the bit is inserted into the bore, the at least one bit face abuts one of the at least two bore faces to force the needle into one of first or second rotational positions relative to the long axis thereof, which are rotated from one another by a degree substantially similar to that of the at least two bore faces.

6. The specimen handling apparatus according to claim 5, wherein the at least one bit face is forced to securely abut the one of the at least two bore faces when the bit is inserted into the bore.

7. The specimen handling apparatus according to claim 5, further comprising a locking element to at least temporarily lock the bit in the bore.

8. The specimen handling apparatus according to claim 5, wherein the body has first and second opposing faces and the bore is defined to extend from the first to the second face, and wherein the needle is substantially straight along the long axis thereof.

9. The specimen handling apparatus according to claim 5, wherein the tip portion is tapered.

10. The specimen handling apparatus according to claim 5, further including reference marks on the body and the needle.

11. The specimen handling apparatus according to claim 5, wherein the first and second rotational positions are rotated one of 90°, 60° or 45° from one another.

12. The specimen handling apparatus according to claim 5, wherein the bore permits incremental rotation of the bit.

13. A specimen handling apparatus, comprising:
a body in which a bore is defined; and
a needle having a tip portion and a bit, which is removably insertible into the bore with the tip portion at least partially exposed,
the bore being formed with at least two faces whose respective planes define a crossing that extends substantially in parallel with a long axis of the needle, and
the bit being formed with at least one face such that, when the bit is inserted into the bore, the at least one bit face abuts one of the at least two bore faces to force the needle into one of first or second rotational positions relative to the long axis thereof, which are rotated from one another by a degree substantially similar to that of the at least two,
wherein the respective abutments of the at least one bit face and the one of the at least two bore faces is a face-to-face abutment.

14. A specimen handling apparatus, comprising:
a body in which a bore is defined; and
a needle having a tip portion, a bit, which is removably insertible into the bore with the tip portion at least partially exposed, and a flange to abut the body when the bit is inserted into the bore,
the bore being formed with at least two faces whose respective planes define a crossing that extends substantially in parallel with a long axis of the needle, and
the bit being formed with at least one face such that, when the bit is inserted into the bore, the at least one bit face abuts one of the at least two bore faces to force the needle into one of first or second rotational positions relative to the long axis thereof, which are rotated from one another by a degree substantially similar to that of the at least two bore faces.

15. A specimen handling apparatus, comprising:
a body in which a bore is defined; and
a needle having a tip portion and a bit, which is removably insertible into the bore with the tip portion at least partially exposed,
the bore being formed with at least two faces whose respective planes define a crossing that extends substantially in parallel with a long axis of the needle, and
the bit being formed with at least one face such that, when the bit is inserted into the bore, the at least one bit face abuts one of the at least two bore faces to force the needle into one of first or second rotational positions relative to the long axis thereof, which are rotated from one another by a degree substantially similar to that of the at least two bore faces,
wherein the bore permits incremental rotation of the bit, and
further comprising:
elastic elements coupled to the bore faces; and
ball bearings to rotatably support the needle.

16. A method of operating a specimen handling apparatus, comprising:
removably inserting a multifaceted bit of a needle into a multifaceted bore of a body such that the needle occupies a first rotational position defined by a flush abutment of at least one bit face and at least one bore face and such that a tip portion of the needle remains exposed;
determining an initial position of the tip portion;
rotating the needle about a long axis thereof such that the needle occupies a second rotational position defined by a flush abutment of at least one bit face and at least one other bore face and such that the tip portion remains exposed; and
verifying that a final position of the tip portion is substantially similar to the initial position.

17. The method according to claim 16, further comprising attaching a specimen to the tip portion, wherein the determining comprises determining an initial position of the specimen and the verifying comprises verifying that a final position of the specimen is substantially similar to the initial position.

18. The method according to claim 16, further comprising removing the multifaceted bit from the multifaceted bore prior to the rotating.

19. The method according to claim 16, wherein the rotating is achieved with the multifaceted bit inserted in the multifaceted bore.

* * * * *